(12) United States Patent
Xiang et al.

(10) Patent No.: US 7,945,335 B2
(45) Date of Patent: May 17, 2011

(54) REMOTELY RF POWERED CONFORMABLE THERMAL APPLICATORS

(75) Inventors: Xiao-Dong Xiang, Danville, CA (US); Gang Wang, Martinez, CA (US); Haitao Yang, San Jose, CA (US); Jonathan Melman, San Mateo, CA (US); Gerald Francis Dionne, Winchester, MA (US)

(73) Assignee: Intematix Corporation, Fremont, CA (US)

( * ) Notice: Subject to any disclaimer, the term of this patent is extended or adjusted under 35 U.S.C. 154(b) by 1124 days.

(21) Appl. No.: 11/601,083

(22) Filed: Nov. 16, 2006

(65) Prior Publication Data
US 2007/0168001 A1 Jul. 19, 2007

Related U.S. Application Data (60) Provisional application No. 60/737,987, filed on Nov. 17, 2005.

(51) Int. Cl.
*A61F 2/00* (2006.01)

(52) U.S. Cl. ........................................ 607/101; 607/102

(58) Field of Classification Search .......... 607/101–103; 977/911; 424/9.323, 9.34
See application file for complete search history.

(56) References Cited

U.S. PATENT DOCUMENTS

| 2005/0118102 | A1 | 6/2005 | Xiang | |
| 2005/0149169 | A1* | 7/2005 | Wang et al. | 623/1.15 |
| 2005/0255046 | A1* | 11/2005 | Zhong et al. | 424/9.34 |
| 2006/0147381 | A1* | 7/2006 | Jones et al. | 424/9.323 |

OTHER PUBLICATIONS

International Search Report and Written Opinion dated Aug. 15, 2007 for Application No. PCT/US2006/044672, 6 pages.

* cited by examiner

*Primary Examiner* — Roy D Gibson
(74) *Attorney, Agent, or Firm* — Fliesler Meyer LLP (57) ABSTRACT

Embodiments of the present invention are generally related to apparatus and methodology of thermal applicators in cancer therapy. In particular, the present embodiments are directed to a technique called "nanoparticle ferromagnetic resonance heating," where ferromagnetic resonance heating in addition to an RF hyperthermia treatment is used to cause cell apoptosis and necrosis. An apparatus for carrying out a ferromagnetic resonance heating treatment of a tumor, comprises a volume concentration of super paramagnetic particles contained within the interior of the tumor, the concentration ranging from about 0.1 to about 1 percent; a magnetic field source configured to deliver a gradient DC magnetic field to the region of the tumor; and an energy source configured to deliver to the tumor an RF field at a frequency ranging from about 100 to 200 MHz. The apparatus of claim 1, wherein the super paramagnetic particles are selected from the group consisting of maghemite ($\gamma$-$Fe_2O_3$) based compounds, and yttrium iron garnet ($Y_3Fe_5O_{12}$) based compounds.

2 Claims, 10 Drawing Sheets

REMOTELY RF POWERED CONFORMABLE THERMAL APPLICATORS

REFERENCE TO RELATED APPLICATION

The present application claims benefit of and priority to U.S. Patent application Ser. No. 60/737,987, filed Nov. 17, 2005 and titled "Remotely RF powered conformable thermal applicators," which is incorporated herein in its entirety for all purposes.

FIELD OF THE INVENTION

Embodiments of the present invention are generally related to apparatus and methodology of thermal applicators in cancer therapy. In particular, the present embodiments are directed to a technique called "nanoparticle ferromagnetic resonance heating," where ferromagnetic resonance heating in addition to an RF hyperthermia treatment is used to cause cell apoptosis and necrosis.

BACKGROUND OF INVENTION

Current cancer therapies, including both radiation and chemotherapy, have serious side effects and limited efficacy, and they may display the phenomenon of resistance to the previous treatment method upon recurrence. Thermal therapies, such as hyperthermia and thermal ablation, both in conjunction with known treatment regimes or as stand-alone treatments, have emerged as promising therapeutic methods. Numerous phase II and III human clinical trials have been conducted as co-treatments together with radiation and chemotherapy, and these trials demonstrated an enhancement of therapeutic effect by 13 to 42 percent. Hyperthermia clinical trials at Duke University's Comprehensive Cancer Center were highlighted in the Summer 2005 Newsweek Special Edition on the Future of Medicine.

The state of the art hyperthermia treatment uses a phase array antenna with radio frequencies ranging from 75 to 900 MHz. It is well established in the art that the preferential heating of tumor tissues is achieved primarily due to reduced blood flow out of diseased tissues. This effect has caused cancer cells to be more susceptible to radiation or chemotherapy. However, this small temperature difference (a few degrees) alone is not enough to cause predominate cancer cell apoptosis while keeping healthy cells intact.

What is needed in the art is the ability to selectively heat a small portion of a tumor beyond the level that can be attained by current hyperthermia treatments, subsequently causing an apoptotic or necrotic response, while simultaneously maintaining a safe temperature in the remaining portions of the tumor (to prevent shock syndrome) and the healthy tissues surrounding the tumor as a valuable pathway to treat cancer. Embodiments of the present invention utilize ferromagnetic resonance heating (FMRH) of tumor-delivered super-paramagnetic (SPM) nanoparticles to provide this additional heating with an image guided surgical precision.

SUMMARY OF THE INVENTION

Embodiments of the present invention are generally related to apparatus and methodology of thermal applicators in cancer therapy. In particular, the present embodiments are directed to a technique called "nanoparticle ferromagnetic resonance heating," where ferromagnetic resonance heating in addition to an RF hyperthermia treatment is used to cause cell apoptosis and necrosis.

An apparatus for carrying out a ferromagnetic resonance heating treatment of a tumor, comprises a volume concentration of super paramagnetic particles contained within the interior of the tumor, the concentration ranging from about 0.1 to about 1 percent; a magnetic field source configured to deliver a gradient DC magnetic field to the region of the tumor; and an energy source configured to deliver to the tumor an RF field at a frequency ranging from about 100 to 200 MHz. The apparatus of claim 1, wherein the super paramagnetic particles are selected from the group consisting of maghemite ($\gamma$-$Fe_2O_3$) based compounds, and yttrium iron garnet ($Y_3Fe_5O_{12}$) based compounds.

Using such an apparatus, a temperature increase of merely 3 to 5 degrees C. is contemplated to add sufficient additional heat to a conventional RF hyperthermia treatment to cause cell apoptosis. Alternatively, a temperature increase of about 7 to 10 degrees C. may lead to non-invasive thermal ablation of cancer cells, such cell death called necrosis.

The present apparatus and techniques allow the temperature of the tumor or cancerous region to be raised by about 6 degrees C. within about 10 seconds. Ferromagnetic resonance heating works in conjunction with an RF field that is already capable of heating the tumor to about 42 degrees C., the additional 6 degrees C. raising the tumor temperature to nearly 50 degrees C. for a short period of time.

BRIEF DESCRIPTION OF THE DRAWINGS

FIG. 2 is an illustration of a magnetic field selected FMR region.

DETAILED DESCRIPTION OF THE INVENTION

Cancer Heat Therapy

Traditional cancer therapies are widely known for their harsh side effects. To reduce these side effects and improve the effectiveness of chemotherapy and radiotherapy commonly used in cancer treatments, less invasive therapies including hyperthermia and thermal ablation have emerged as safer and more effective technologies. Hyperthermia may be defined as the heating of an organ(s) and/or tissue(s) to temperatures between about 41° C. and about 46° C., which reduces the viability of cancer cells and increases their sensitivity to chemotherapy and radiotherapy. Thermal ablation may be defined as the heating of a tumor(s) to even higher temperatures (about 49° C. to about 56° C.), causing necrosis, coagulation, or carbonization of the tumor cells.

There are several mechanisms by which a stand alone hyperthermia treatment may function. The prevailing thought is that elevated temperature (between about 44° C. to about 48° C.) alters the function of the proteins within cells, which in turn can affect cell growth and cell differentiation. In many cases apoptosis may be induced, which is a programmed cell death. When used in conjunction with conventional treatments, hyperthermia has been shown to increase efficacy by enhancing the perfusion, vascular permeability and oxygenation caused by conventional chemotherapy and/or radiation treatments.

Conventional hyperthermia techniques involve heating cancer cells from outside the cells. Various methods ranging from hot baths, wax encasement, induced fevers, local perfusion of extremities with heated chemotherapeutic agents, diathermy, radio-frequency, microwave heating to ultrasound heating have been attempted in the past.

All clinical hyperthermia trials have used these extracellular methods and consist of three different approaches: whole body hyperthermia (WBH), regional hyperthermia (RHT), and local hyperthermia (LHT). Successful LHT and RHT techniques rely on the targeting and the directing the heat toward cancer cells, hopefully with an accurate control of temperature distribution. LHT and RHT are commonly performed using radio-frequency, microwave, or ultrasound applicators. The state-of-the-art hyperthermia system is the annular phased array system (APAS), in which microwave antennae are arranged cylindrically around the axis of the body to focus the electromagnetic field on a region with a typical diameter of about 10 cm (depending on the frequency of the microwave radiation).

In addition, annular phased array systems for the regional hyperthermia of deeply seated tumors is limited by the heterogeneity of tissue electrical conductivities and of highly perfused tissues (these heterogeneities being well known in the art), which makes selective heating of those regions difficult. Much of the heating in these techniques is dependent upon the difference in vasculature between healthy and diseased tissues. Blood flow can assist cooling when the vasculature is ordered, and does not restrict the flow of blood out of the region as is the case in healthy tissue. Diseased tissue, especially in larger tumors, has chaotic vasculature which is not conducive to blood flow out of the tumor. This effect causes cancer cells to reach higher temperatures than healthy cells. This small temperature difference (typically only a few degrees) can cause cancer cells to be more susceptible to subsequent radiation and/or chemotherapy treatment, but is not enough by itself to cause predominate cancer cell death while keeping healthy cells intact.

A number of Phase II studies have examined hyperthermia as a co-treatment with chemotherapy. Phase III clinical trials have shown that when used on appropriate tumor systems, hyperthermia in conjunction with radiation treatment showed a 13 to 42 percent increase in complete response rate. Even the negative trials, when broken down into appropriate subsets showed some efficacy.

Magnetic nanoparticle based hyperthermia using the Néel heating mechanism has been studied over last 26 years. The mechanism behind Néel heating is that a small single domain magnetic particle can relax (re-orient) its magnetization direction polarized by an external magnetic field through a thermal process; in other words, thermal energy is sufficient to re-orient the magnetization of a small magnetic domain. The observation of specific uptake of magnetic nanoparticles by cancer cells raised the potential for specific killing of cancer cells. Direct, arterial and intravenous injection mechanisms have all shown good delivery of magnetic nanoparticles to cancerous tissues, including mammary tumors, glioblastoma as well as colorectal, ovarian, cervical and prostate carcinomas and sarcomas. This technique has been studied as an alternative to external source hyperthermia. The advantage of this technique over the phase array antenna is that of more uniform heating of the tumor. The shortcoming is the required high concentration of nanoparticles. Magnetic particle hyperthermia has not shown high efficacy as a stand-alone treatment, but has achieved results as a co-treatment, similar to conventional hyperthermia.

The present inventors contemplate the ability to selectively heat a portion of tumor beyond the level attained by hyperthermia treatment as a valuable method of treating cancer. Selectively heating may subsequently cause predominant cancer cell death in the region, while maintaining a safe temperature in the remaining portions of the tumor and in the healthy tissues surrounding the tumor. Maintaining a safe temperature environment in the portions of the tumor not being selectively heated is necessary to prevent shock syndrome. In the present embodiments, ferromagnetic resonance heating (FMRH) of tumors containing nanoparticles (or micro-particles) is used to provide the required additional heating with an image guided surgical precision.

FMRH in Conjunction with Hyperthermia Treatments

Figure 1:
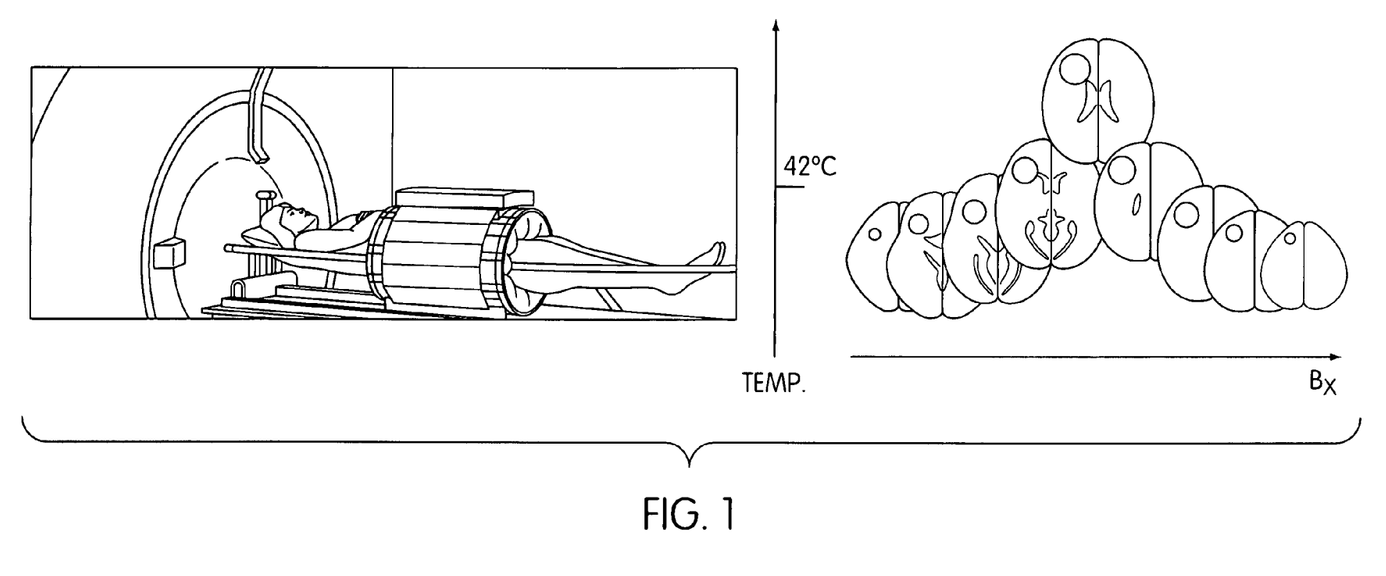
FIG. 1 schematically illustrates slice by slice heating of a tumor on top of a hyperthermia temperature using FMRH.

The present technique of ferromagnetic resonance heating (FMRH) is carried out with an RF field that uses substantially the same frequencies as prior art phase array antenna systems; e.g., about 100 to about 200 MHz, inclusive. By applying a gradient DC magnetic field similar to those in MRI systems, nanoparticles with optimized ferromagnetic resonance parameters will be heated above the hyperthermia temperature to a thermal ablation regime, in a slice by slice fashion, as illustrated in FIG. 1. In the present treatment configuration, which may be termed "nanoparticle FMRH," a temperature increase of merely about 3 to 5 degrees C. will add sufficient additional heat to the RF hyperthermia treatment temperature to cause apoptosis. Alternatively, a temperature increase of about 7 to 10 degrees C. can lead to non-invasive thermal ablation of cancer cells (necrosis). Such technology is able to replace currently used radiation and/or chemotherapy techniques, thus eliminating the serious side effects associated with radiation and/or chemotherapy. The present inventors contemplate that the nanoparticle FMRH technique will provide enhanced tools and methodologies that may be applied to the fight against cancer.

Additional advantages and attractive features of FMRH include, but are not limited to:

1. Heating efficiency
   a. Therapeutic temperatures achievable on a rapid time scale;

b. The FMRH mechanism is not dependent on particle size, so that different sizes of particles may be selected for different delivery methods and/or targets
2. Imaging
a. Traditional imaging techniques (i.e., magnetic resonance imaging, or MRI, and computerized tomography, or CT) can locate particles for targeted treating; but
b. Similar particles can be used as thermometry to monitor and control treatment temperatures in those techniques The spin relaxation time scale of maghemite ($\gamma$-$Fe_2O_3$) based compounds, and/or yttrium iron garnet (YIG, $Y_3Fe_5O_{12}$) families of compounds, are ideally suited for use in the present FMRH techniques. The present inventors have used realistic parameters to estimate dielectric and FMR heating effects. The results show that heating from ferromagnetic resonance (FMR) is more than about three orders of magnitude greater than that which may be achieved with conventional dielectric heating. This implies that a nanoparticle volume concentration of only about 0.1 to about 1 percent is required to achieve the differential heating described above, a concentration which is far lower than the required concentration for a Néel heating based hyperthermia treatment. The magnetic field that was assumed in these calculations was 0.08 Gauss (about 6 A/m), which is well within the safety guidelines currently set forth for MRI. The present inventors have performed experiments which give results consistent with an estimated power absorption intensity for doped-YIG materials, confirming the FMRH effect in a phantom system. Furthermore, the concept of precise localized heating has been demonstrated by control of the DC magnetic field.

Ferromagnetic resonance and heating effect measurements of nanoparticles of the same materials (fabricated using Intematix Corporation's proprietary combinatorial laser pyrolysis system) may be performed after surface coating and suspension in the biocompatible solution. Prior art toxicity studies have indicated that aminopropylsilane coated YIG systems are biocompatible and non-toxic. The present inventors have undertaken separate studies related to toxicity issues.

The Mechanism of Ferromagnetic Resonance Heating

Although the mechanism according to which ferromagnetic resonance (FMR) operates is similar to that of either nuclear magnetic resonance (NMR) or electron spin resonance (ESR), FMR is a far more powerful and versatile heating method. In NMR and ESR, resonance occurs when the frequency of the microwave and/or RF radiation, the externally applied magnetic field, and the material's gyromagnetic ratio all satisfy the following equation:

$$h\nu = g\mu B \quad (1)$$

where h is Plank's constant, $\nu$ is the magnetic spin resonance frequency, B is the external DC magnetic field, g is the Landre factor, and $\mu$ is either the nuclear magneton $\mu_N$ for nuclear magnetic resonance (NMR) or the Bohr magneton $\mu_B$ for electron spin resonance (ESR). Nuclear spins or electron spins absorb photon energy (from the RF or microwave radiation) at the spin resonance and jump to a higher energy level, all the while precessing coherently. As the spin precessing relaxes through a spin-lattice interaction, the absorbed electromagnetic energy is converted to heat. The heat generation is inversely proportional to the relaxation time, and proportional to the density of the unpaired spins and the spin population difference (meaning the difference in populations of the excited and un-excited states). The spin population difference $\Delta n$ in two adjacent Zeeman levels at room temperature is governed by Boltzmann statistics:

$$\Delta n = 1 - \exp\left(-\frac{h\nu}{kT}\right) \quad (2)$$

Since the energy difference between two Zeeman levels is small, thermal excitation at elevated temperature causes spins to occupy both energy levels in substantially equal numbers, leaving only a very small fraction of spins to contribute to the spin resonance. At room temperature and in a 5 T magnetic field, this corresponds to a factor of $10^{-5}$ reduction in resonance absorption for a typical NMR. The same is true for paramagnetic electron spin resonance if the excitation frequency is the same as in NMR (a necessary condition if such radiation will be penetrating a human body). This explains why normal nuclear spin resonance (NMR) and electron paramagnetic resonance (EPR) absorptions are not effective in generating heat for therapeutic applications. In addition, nuclear spin resonance absorption heats up most if not all of the protons in the sample, which is not suitable for a targeted therapeutic treatment in humans.

Very efficient heating may be achieved using ferromagnetic resonance absorption of super paramagnetic (SPM) nanoparticles. SPM particles are ferromagnetic particles (or materials) with substantially no magnetic coercivity or spontaneous magnetization. In the absence of an applied magnetic field, the particles do not exhibit magnetization and there is no magnetic force between them. As a consequence, they do not interact magnetically with one another, such as clumping together in the absence of an applied magnetic field. This ensures that the particles can be suspended uniformly in biocompatible solutions, delivered to a cancerous region, and ingested by the cancer cells being targeted before the treatment field is applied. In the presence of an applied DC magnetic field, however, the spins of unpaired electrons in these particles are correlated and the particles are magnetized. As a result, under the ferromagnetic resonance conditions, all unpaired electron spins will be excited, rather than only $10^{-5}$ of the total unpaired in NMR or ESR ($10^{-5}$ being the population difference between the excited and un-excited spin energy states).

Theoretically estimated heat absorption of magnetic nanoparticles at ferromagnetic resonance is $10^2$ to $10^3$ times more efficient than that of Néel heating. Assuming a uniform distribution of nanoparticles, the temperature of a tumor or cancerous region may be raised by about 6° C. within about 10 seconds, as will be shown by a calculation later in this disclosure. As FMRH works in conjunction with an RF field already capable of heating the tumor to about 42° C., the additional 6° C. can raise the tumor temperature to nearly 50° C. for a short period of time. Healthy tissues are maintained at temperatures below 40° C., a highly desirable effect. Thus deep seated, targeted, thermal ablation may be realized in a slice by slice manner throughout the desired region.

For ferromagnetic materials, spin resonance occurs only in materials having a single domain; i.e. the magnetization is saturated ($M=M_s$) when the applied magnetic field exceeds a certain field strength. The saturation magnetization is related to the composition of bulk materials. Since mono-dispersed nanoparticles are single domain entities with negligible interactions, no ensemble saturation is required and the spin resonance condition will be satisfied for each particle. This has been confirmed by several experiments. In the case of a single domain magnetic nanoparticle, the spin resonance depends only on the applied magnetic field and should have no lower bound. Optimized nanoparticles for such an application will have the highest magnetization at the applied field (about 100-200 Gauss), and relaxation times on the order of about 1 μs.

Magnetic nanoparticles with surface chemical modifications have been used in the art for various medical applications and therapeutic treatments. The surface characteristics of SPM particles may be optimized to further enhance the differential uptake of the particles by cancer cells versus uptake by normal cells. Prior art studies have shown that magnetite coated with a variety of materials is non-toxic in human fibroblasts. Such coating materials included pullulan, lactoferrin, ceruloplasmin, insulin, poly(ethylene glycol) and albumin) as well as yttrium aluminum iron garnet (more specifically the aluminum doped YIG) coated with an aminopropylsilane.

Internal Thermometry and Image Guiding

Figure 2A:
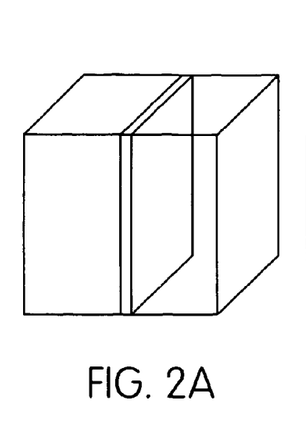
FIG. 2A illustrates a constant $H_0$ plane selection.
Figure 2B:
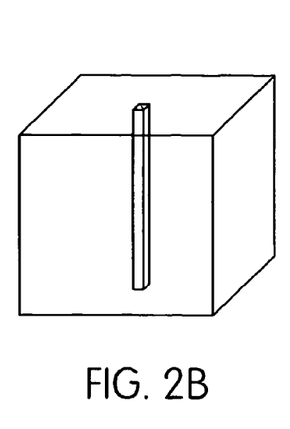
FIG. 2B illustrates a constant $H_0$ line selection.
Figure 2C:
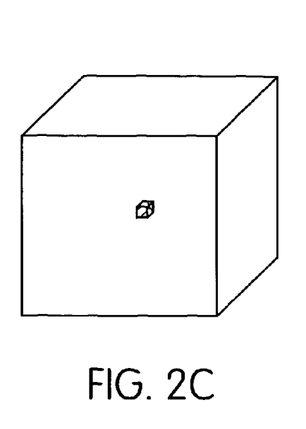
FIG. 2C illustrates a constant $H_0$ point selection.

Compared with Néel heating and dielectric heating, one of the most important advantages of FMR heating is the potential of having selective activation. FMR heating only happens when the conditions of Eq. (1) are met, particularly (for the purposes of this discussion), the value of the local DC magnetic field that satisfies the equation. A common technique in the art is to design a magnet system capable of providing different magnetic fields at different locations. For example, assuming that $H_0$ is the value of the local magnetic field dictated by Eq. (1), then the shape of the region of constant $H_0$ includes, but is not limited to, any one of the situations illustrated in FIGS. 2A-2C. The region of constant $H_0$ could be shaped a surface, as illustrated in FIG. 2A; a line, as illustrated in FIG. 2B, or a point (or spot), as illustrated in FIG. 2C. Additionally, it is not necessary to have a flat shape for the surface in FIG. 2A, nor does the shape of the line in FIG. 2B have to be straight. In other words, the surface and the line in FIGS. 2A and 2B, respectively, may be curved in 3D space. It is this ability to spatially select the shape of the local DC magnetic field (among other reasons) that renders FMR heating to be more flexible and thus have greater advantages than either Néel heating or dielectric heating.

Figure 3:
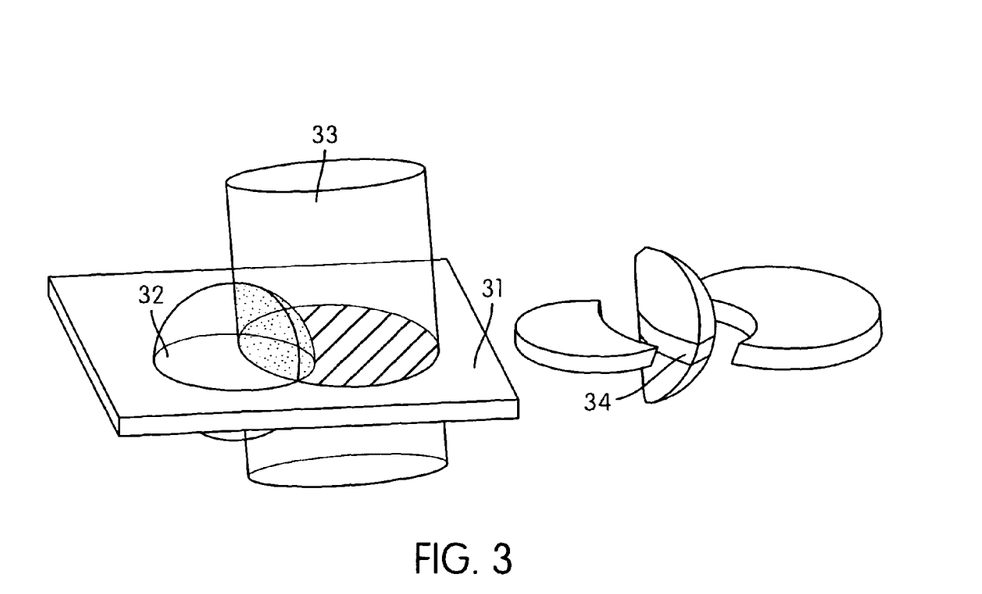
FIG. 3 is an illustration of selective FMR heating at the intersection of the $H_0$ plane, the particle concentrated region, and the RF field intense region.

In addition to magnetic field selection (the technique of selecting the shape of the magnetic field), the distribution of the RF field and the nanoparticles provides another way to achieve spatial selective heating. As illustrated in FIG. 3, it is the intersection of the $H_0$ slice 31, the particle concentrated region 32, and the RF field intense region 33 that may be controlled and/or adjusted to achieve the desired FMR heating in an effective heating region 34.

Additional advantages are that ferromagnetic electron spin resonance frequencies of the nanoparticles may be used to monitor the temperature of the particles (and therefore the cells as well), quite literally qualifying as a technique of internal thermometry, because of the temperature dependence of ESR properties in super-paramagnetic nanoparticles. One such property of ferri- (e.g., YIG family) or ferromagnetic materials is that saturation magnetization depends on temperature. It has been previously demonstrated in the art that such an effect may be used to measure temperature with a sensitivity of 1° C. The present inventors contemplate utilizing this effect to control temperature.

In contrast to a conventional nuclear magnetic resonance (NMR) based magnetic resonance imaging (MRI) imaging facility that uses super paramagnetic particles (SPM) as $T_2$ contrast agents, electron spin resonance (ESR) based imaging of SPM particles is contemplated in the present embodiments, such that heat treatment, imaging, and internal thermometry may each be accomplished with the same equipment, and at a much lower cost than in the case of conventional MRI. The reason for the lower cost is that the required magnetic field for ESR is very low (less than about 500 Gauss), and much of the cost of an instrument is in the magnet needed to supply the external magnetic field.

The foregoing discussion outlines the tremendous potential that embodiments of the present invention offers to medical science in general, and to cancer therapy treatment methods in particular. With that discussion as an introduction, more of the details will now be disclosed.

Estimation of the Resonance Heating Effect with SPM Particles

According to embodiments of the present invention electromagnetic irradiation excites the ferromagnetic resonance of super paramagnetic (SPM) nanoparticles or microparticles, which in turn heats up the tissue. But dielectric heating also occurs, due to the conductive nature of the tissue. Different from nanoparticle induced heating, dielectric heating occurs in all tissues exposed to the RF field, rather than only the tissues containing SPM particles. For FMR heating to be effective, its heating power must be comparable to or higher than the heating power attributable to dielectric heating. The present inventors have performed calculations to analyze the extent to which heating occurs from these two sources: 1) dielectric heating; and 2) ferromagnetic spin resonance of SPM nanoparticles. Heat transfer calculations have also been made to study the heat transfer process from a nanoparticle to its surrounding environment. As a comparison, the Néel heating and dielectric heating at corresponding working frequency were also analyzed. These results will now be given.

For ferromagnetic power absorption under electromagnetic irradiation, analysis shows that the power absorption per unit volume by SPM nanoparticles, for both ferromagnetic spin resonance and Néel heating, is:

$$P = \frac{\gamma \mu_0^2 M_0 \omega T_2 H_1^2}{1 + (\omega - \omega_0)^2 T_2^2 + T_1 T_2 \gamma^2 \mu_0^2 H_1^2} \quad (3)$$

where γ is the electron gyromagnetic ratio, $M_0$ is the particle saturated magnetization, $\omega_0$ is the ferromagnetic resonance frequency ($\omega_0=0$ for Néel heating), $H_1$ is the RF magnetic field, $\mu_0$ is the vacuum permeability, and $T_1(T_2)$ is the spin relaxation time. A different relaxation scheme exists with Néel heating due to anisotropy energy, such that $T_1(T_2)$ should be replaced by the relaxation time τ. Under conditions of magnetic saturation (which may be defined by the condition $T_1 T_2 \gamma^2 \mu_0^2 H_1^2 \gg 1$), Eq. (3) becomes $$P = \frac{M_0 \omega}{T_1 \gamma} \quad (4)$$

It is a well known effect that a ferromagnetic particle becomes super paramagnetic when it has a size smaller than some critical value. In this case, both retentivity and coercivity are zero. The magnetization of the particle is a function of the local magnetic field. To achieve FMR heating, a low $M_0$ is used to make certain that the resonance exists on the working frequency. A DC magnetic field is applied to ensure that the magnetization reaches its saturation value. For Néel heating, however, no DC magnetic field exists. The magnetization of the particle is fully induced by the RF magnetic field $H_1$. As a result, $M_0$ in Eq. (3) holds true only when $H_1$ is high enough to saturate the magnetization; otherwise, $M_0$ should be replaced by $M=\chi H_1$, where, χ is the magnetic susceptibility of the particle.

On the other hand, dielectric heating is caused by the resistive impedance of the tissue. Under an RF electrical field $E_1$, the power absorption per unit volume in a tissue with relative permittivity $\epsilon'$ and conductivity $\sigma$ is:

$$P = \frac{1}{2}\sigma E_1^2 \quad (5)$$

Under the propagating wave condition (a good approximation for a phase array antenna system), the relationship between the RF electric field $E_1$ and the magnetic field $H_1$ is:

$$H_1 = E_1 \sqrt{\frac{\epsilon_0}{\mu_0}\left(\epsilon'^2 + \frac{\sigma^2}{\omega^2 \epsilon_0^2}\right)^{1/2}} \quad (6)$$

where $\epsilon_0$ is the vacuum permittivity. If a cavity or near field configuration is used in the design of an RF heating applicator, the relationship can be more complex. The ratio of $E_1/H_1$ can change by more than one order of magnitude with designs that differ from that of a near field configuration. This relationship still holds for the phase array antenna, however, a configuration commonly used in previously known hyperthermia systems.

According to Eqs. (5) and (6), the maximum applicable $H_1$ that may be applied to a specific tissue and/or material can be calculated due to the limitation of the dielectric heating. One commercial hyperthermia system, for example, produces a typical heating power of about $P_0=15\times10^4$ W/m$^3$ to heat tissue to a temperature of about 40° C. to about 45° C. for 30 to 40 minutes. The magnetic field $H_1$ at this power determines the absorption power of the FMR and Néel heating.

Figure 4A:
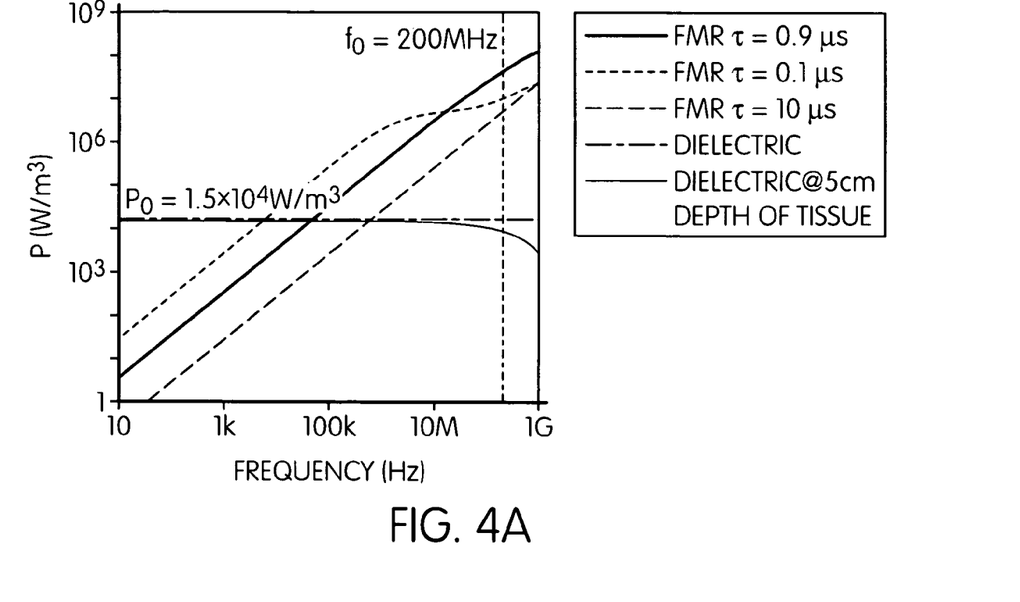
FIGS. 4A and 4B are power absorption density curves of (A) FMR, and (B) Néel and dielectric heating (horizontal line in FIGS. 4A and 4B caused by RF electrical field) as function of RF frequency, assuming that Eq. (6) holds.
Figure 4B:
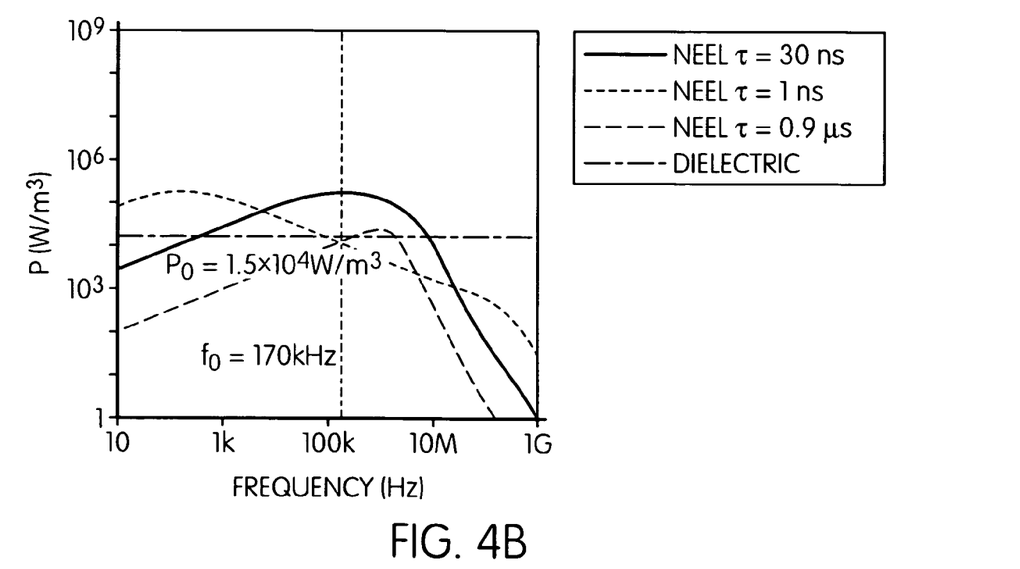

FIGS. 4A and 4B show the three types of power absorption in breast fat tissue as function of RF frequency. The relative permittivity $\epsilon'$ and conductivity $\sigma$ of breast fat is a function of frequency as well, which has been reported in the prior art detail. To achieve an optimized power absorption rate, the saturation magnetization $M_0$ in FMR heating would be 8000 A/m at a frequency of about 200 MHz, and it is proportional to f at other frequencies. Since $H_1$ is not high enough in Néel heating to saturate super paramagnetic particles, the expression $M=\chi H_1$ is used, where $\chi=11$ is the best reported value for typical super paramagnetic particles. FIG. 4A shows that power absorption increases with frequency with FMR heating (the two dielectric heating curves being substantially horizontal throughout most of the frequency range), while the Néel heating shown in FIG. 4B demonstrates a maximium power absorption in the range of from about 100 kHz to about 1 MHz, the particular value of the maximum being determined by the relaxation time τ. Due to the limitation of the penetration depth at higher RF frequencies, the FMR heating frequency is generally not desirable to be greater than about 200 MHz.

The solid horizontal line in FIG. 4A shows the exponential decrease of RF power at a depth of about 5 cm inside the breast fat tissue. Further optimized results of FMR and Néel heating can be calculated by comparing the power absorption of at different relaxation times. To simplify the calculation, $\tau=T_1=T_2$ was used in the present calculation. By comparing the power absorption of FMR at $\tau=10$, 0.9 and 0.1 μs, illustrated in FIG. 4A, the maximum power absorption was found to occur at about 200 MHz when $\tau=0.9$ μs. Similarly, by comparing the power absorption of FMR at $\tau=1$ ns, 30 ns and 0.9 μs as shown in FIG. 4B, the power absorption of the Néel heating was found to reach a maximum at about 170 kHz when $\tau=30$ ns.

The relaxation time $T_1(T_2)$ of FMR is determined by the properties of the material. A relaxation time of about 0.9 μs is a typical value for common FMR materials such as $\gamma$-Fe$_2$O$_3$ or YIG. In contrast, the relaxation time τ with Néel heating is determined by the ratio of anisotropy energy KV to the thermal energy kT:

$$\tau=\tau_0 e^{KV/kT} \quad (7)$$

where $\tau_0$ is about 1 ns, V is the volume of the particle, T is the temperature, k is the Boltzmann constant, and K is the shape anisotropy energy density. The 30 ns relaxation time can be achieved by reducing the particle size to several nanometers, or by decreasing the aspect ratio of the ellipsoids. However, the reduced size or aspect ratio may also decrease the saturation and susceptibility of the particles, which in turn decreases the power absorption of the Néel heating.

Figure 5:
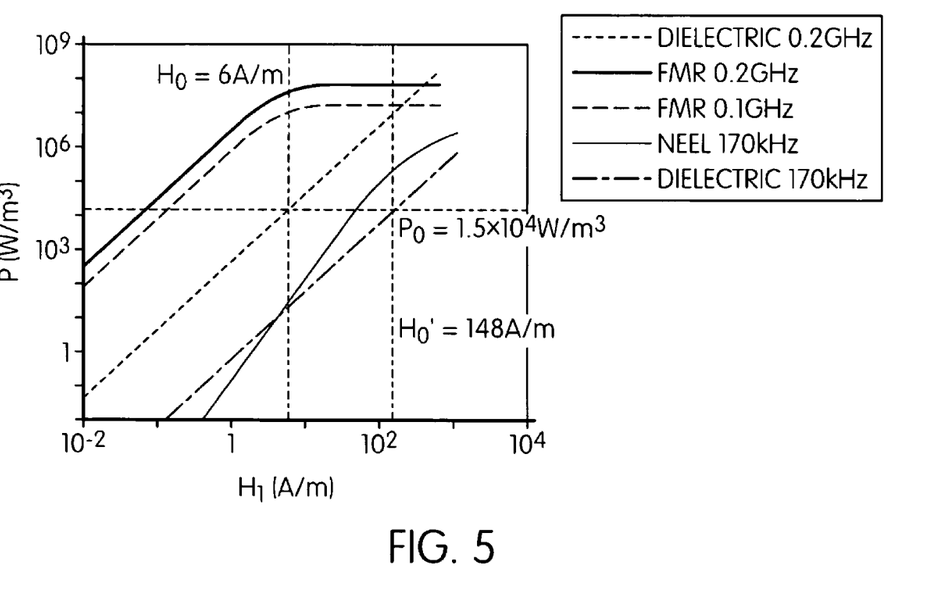
FIG. 5 is a power absorption density curve of FMR, Néel and dielectric heating (caused by RF electrical field) as function of an RF magnetic field, again assuming that Eq. (6) holds.

When the desired parameters have been optimized, the power absorption of the FMR and Néel heating may be compared at different magnetic fields. These results are shown in FIG. 5. One of ordinary skill in the art may see from FIG. 5 that the power absorption of FMR heating and dielectric heating is proportional to $H_1^2$ when the magnetic field is small, while the power absorption of Néel heating is proportional to $H_1^3$ (also for small magnetic fields). As $H_1$ increases, the power absorption of the FMR heating saturates at about $6.3\times10^7$ W/m$^3$. On the other hand, the power absorption of the Néel heating continued to increase at relatively high fields, becoming substantially linearly proportional to $H_1$.

When the level of the magnetic field $H_1$ is sufficiently large to saturate the magnetization of a nanoparticle, the power absorption of the Néel heating saturates as well (not shown in the figure). By using $M_0=4.7\times10^5$ A/m (roughly 60 times higher than that used for FMR heating), the saturation power is $9.5\times10^7$ W/m$^3$, which is similar to the value seen with FMR heating. However, the RF magnetic field has to be higher than 40 kA/m, which is difficult to achieve with current technologies. In addition, dielectric heating does not have a saturation limitation. At high magnetic fields, the power absorption of dielectric heating will exceed both that of FMR and Néel heating.

In one embodiment of the present invention, heating is achieved first by heating up a large volume through dielectric heating, and then heating a specific region filled with nanoparticles to an even higher temperature, this additional heating accomplished via FMR. One set of results is given in FIG. 5, which shows the maximum power absorption of FMR and Néel heating under the RF filed when the power absorption of dielectric heating is $1.5\times10^4$ W/m$^3$. The results are listed numerically in Table 1.

TABLE 1

Power absorption and required magnetic field of FMR and Néel heating under the same dielectric heating power of $P_0 = 1.5 \times 10^4$ W/m$^3$

| Power absorption density | P (W/m$^3$) | Ratio P/P$_0$ | H$_0$ (A/m) |
|---|---|---|---|
| FMR heating @ 0.2 GHz | $3.7 \times 10^7$ | $2.5 \times 10^3$ | 6.0 |
| FMR heating @ 0.1 GHz | $1.1 \times 10^7$ | $7.3 \times 10^2$ | 7.2 |
| Néel heating @ 170 kHz | $1.7 \times 10^5$ | 11 | 150 |

Table 1 illustrates that at a working frequency of 200 MHz, the power absorption of FMR is $2.5\times10^3$ higher than that of dielectric heating. This allows an FMR treatment to be effective at concentrations as low as 0.1 percent, recognizing that higher concentrations may also be used if it is desired to operate using shorter treatment times. Because of issues related to penetration depth, FMR heating is still 730 times greater than dielectric heating when the working frequency is decreased to 100 MHz, with the FMR technique effectively heating up tissue even at a 1 percent particle concentration. The power absorption of Néel heating is only 11 higher than the dielectric heating, and here the concentration needs to be greater than 10 percent for the absolute power absorption to exceed that for the RF hyperthermia case.

It is important to note that all the above calculations are based on the propagating wave assumption expressed in Eq. (6), which is adequate for a phase array antenna system. When a Rabin's macro-scale model is adopted, the temperature increase in a region with uniformly distributed particles under steady state is:

$$\theta_t = \frac{pD_t^2}{8k}, \quad (8)$$

where p is the average power absorption per unit volume in a treated region, $D_t$ is the diameter of the region, and k is water thermal conductivity 0.64 W/m° C. Assuming a nanoparticle volume concentration of 1/30, the minimum required particle-loaded region needs to be about 5 mm in size in order to achieve a 6° C. temperature increase when the heating power is $3.6 \times 10^7$ W/m$^3$.

Calculations were carried out for other types of tissues, such as liver tissue and ovarian tissue, in order to compare differences in power absorption with the results previously obtained for breast fat tissue. These calculations showed that the gain factor for both FMR and Néel heating changed within a factor of 2, which may be attributed to differences in the permittivity and the conductivity of liver and ovarian tissue relative to breast fat tissue. Thus, the present inventors contemplate that FMR heating is applicable to most, if not all types of tissues.

Optimization of the RF Applicators

Further enhancement of therapeutic techniques by using FMR heating in addition to dielectric heating may be achieved through the design of the RF applicator. As mentioned above, the relationship between the RF magnetic field and electric field is given by Eq. (6), which holds when a propagating wave assumption is made. When the RF frequency is equal to or smaller than about 200 MHz, the RF wavelength in a vacuum is larger than about 1.5 m. If the applicator size is around 10 cm and the working distance is around the same scale, than the near field contribution to $E_1$ and $H_1$ is not negligible, and this changes the relationship between $E_1$ and $H_1$. To improve the FMR heating capability, the RF applicator should be able to generate a higher magnetic field without increasing the local electrical field.

Figure 6A:
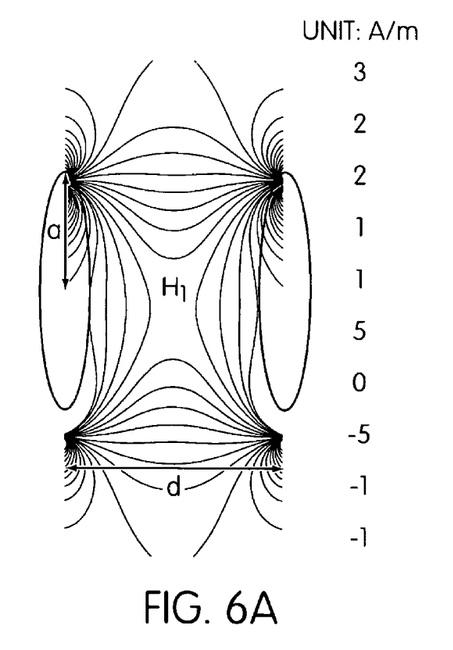
FIGS. 6A-D are simulations of an RF field generated by a pair of Helmholtz coils: a) is a simulation of the magnetic field, $H_1$, and b) is a simulation of the electric field, $E_1$; where c) and d) show three-dimensional views.
Figure 6B:
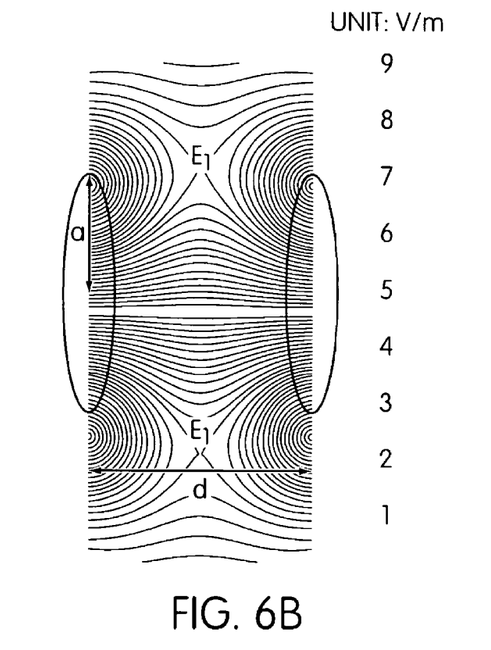
Figure 6C:
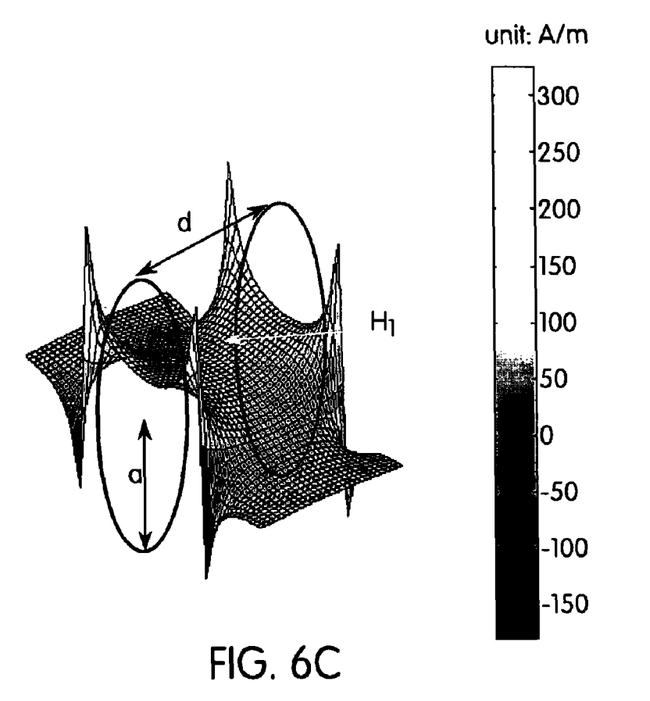
Figure 6D:
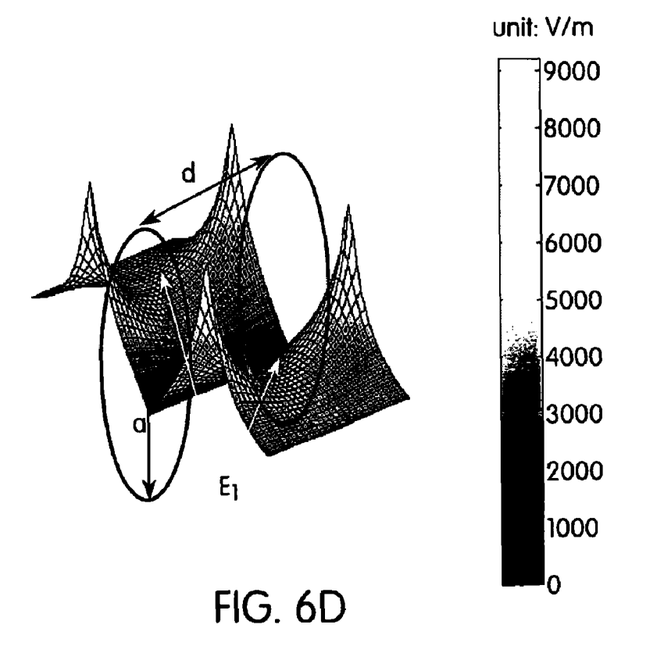

One design parameter which may be used to achieve such a goal is the use of a coil. FIGS. 6A-B show the simulation result of the (a) $H_1$ and (b) $E_1$ field of a Helmholtz pair which contains a pair of coaxial coils with same radius a and distance d. In this type of configuration, the current circulates in the same direction in both coils. The simulation parameters were chosen to be 200 MHz for the RF frequency, 12.5 amps for the coil current, d=2 a=12 cm for the distance between the coils of the pair, and the radius of each coil, respectively. As shown in FIGS. 6C-D, the Helmholtz pair can form a saddle-shaped magnetic field such that the (c) magnetic and (d) electric fields in the central region of the coils are each very uniform.

Figure 7:
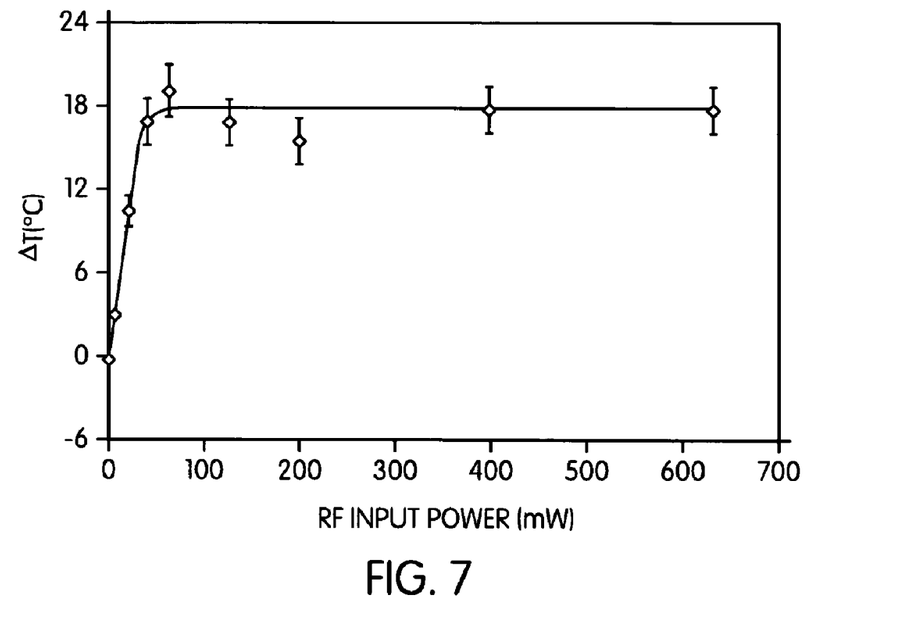
FIG. 7 is a plot of the FMR induced temperature change as function of RF input power.

The average value of $H_1$ in this central, saddle-shaped region is about 74 A/m. The electric field $E_1$ is very different from $H_1$ in that the amplitude of the electric field is zero at the center axis, wherein its value increases gradually to a peak value when the distance to the center axis is close to the coil radius. Along the axis direction $E_1$ is reduced in the middle of the coil pair, and forms a double-saddle region as marked by $E_1$ in FIG. 7D. The average electric field in the saddle region(s) is 2.5 kV/m. Thus, the present inventors were able to calculate a ratio of $H_1/E_1=0.03$.

Previously in this disclosure, it had been stated that the ratio $H_1/E_1$ of a propagating wave is about 0.02 body tissue with a high water content, and 0.003 in vacuum. The ratio of coils is at least 1.5 times better than the case of a propagating wave. When the coil radius is smaller than the wavelength of the RF wave, $H_1/E_1$ is reversely proportional to the ratio of coil radius and wavelength. So this factor can be further improved by decreasing the coil radius, or decreasing the RF frequency. For example, by decreasing the frequency from about 200 MHz to about 100 MHz, the ratio becomes about $H_1/E_1=0.06$, which is 3 times better than that for a propagating wave. Since the power absorption of the FMR technique and the dielectric heating technique is proportional to $H_1^2$ and $E_1^2$, respectively, an increased gain factor may be realized in terms of energy.

Measurement of the Specific Absorption and Heating Rate of a Single YIG Particle FMR heating effect of a single YIG sphere has been studied by the present inventors, the experiment requiring a specially designed setup. A single YIG sphere (having a diameter Φ of about 0.3 mm) was doped with gallium (Ga) to decrease the particle's $M_s$ value from about 1750 to about 250 Gauss, which in turn decreased its FMR frequency. A half-wavelength coaxial resonator with a small field emission coil at one end was used to provide the RF power to stimulate the FMR. The resonant frequency was set to a value of about 487 MHz. The DC magnetic field required for (FMR) resonance was applied in a direction parallel to the surface of the coil using a permanent magnet.

The temperature change of the YIG sphere was determined by measuring the phosphorescence of a europium (III) thenoyl trifluoroacetonate (ETTA) compound coated on the surface of the YIG sphere. A calibration curve of YIG surface luminescence intensity change vs. the temperature was generated by gradually heating the YIG sphere with a hot plate. A thermocouple was positioned in contact with the YIG sphere to ensure the accuracy of measured temperature.

FIG. 7 is a graph of the temperature change (in degrees C.) of the YIG sphere as a function of the RF input power (in mW). Any background effects due to a slight heating from the RF power input were subtracted from the result, using the values measured by changing the DC magnetic field to turn the spin resonance of the YIG particle on and off. FIG. 7 shows that the temperature of the YIG sphere increased rapidly (by as much as 18° C.) as the RF input power was increased to a saturation value of 50 mW.

To measure the RF absorption rate, which in this embodiment will be called the specific absorption rate (SAR) of the YIG particle, the cavity reflection, transmission and loss was measured; these measurements taken with and without FMR absorption by the YIG particle. The FMR absorption by the YIG particle can be directly calculated through the scattering matrix of the resonator.

Figure 8:
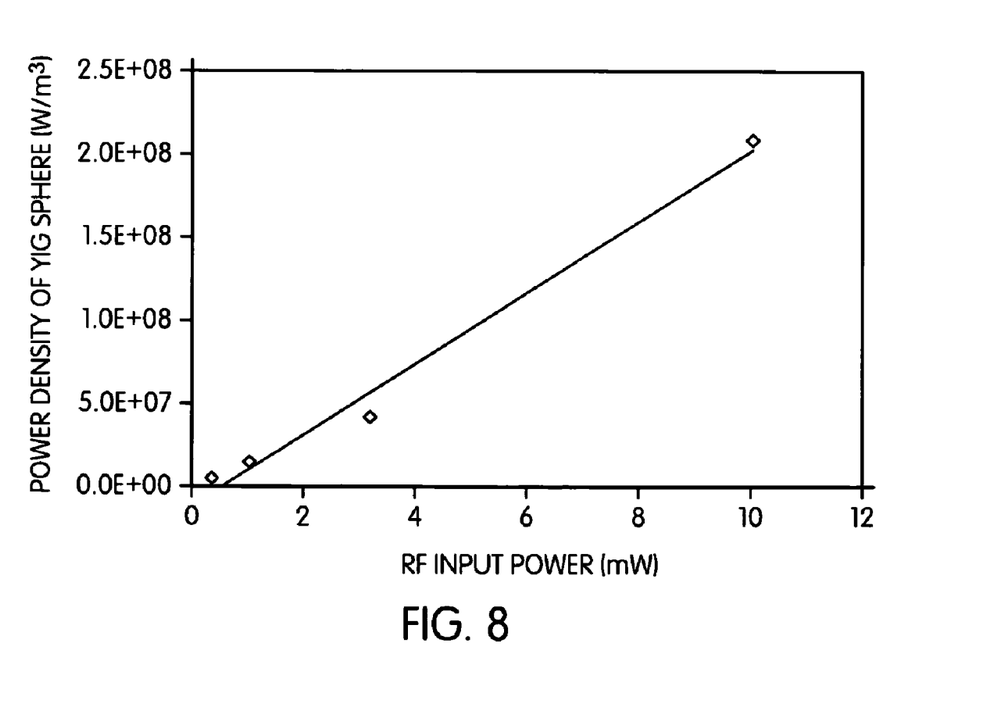
FIG. 8 is a plot of YIG consumed power density at different RF input power levels.

The experiments showed a very sensitive dependence of the heating of the particle on the DC magnetic field, confirming that localized heating by FMR was being controlled by the gradient of the DC magnetic field. The scatter matrix of the resonator was measured by a network analyzer. The measured YIG absorption power density at different RF input powers is shown in FIG. 8. FIG. 8 shows that the spin resonance is not saturated when the RF input power is low, and as a result, the RF power absorbed by the YIG sphere increases linearly until saturation occurs at 50 mW (see again FIG. 7). The saturation power density of the YIG sphere is about $1 \times 10^9$ W/m$^3$, which is given by the slope of the plot in FIG. 8.

Especially pertinent to this disclosure is a consideration of the frequency and field intensity differences between those values obtained using calculations in previous sections of this disclosure, and the experimental results just presented. Such a comparison confirms that the formulism and approximations adopted for the theoretical analysis were correct.

The configuration of the heating experiment just described may also be seen as realistic (meaning close to the conditions that will actually be found in an actual therapeutic application) in that the thermal conductivity of the materials surrounding the YIG sphere is very similar to that of water. The rise in surface temperature in this case is equivalent to that of a 3 percent by volume nanoparticle dispersion in a 1.4 mm diameter spherical region of an infinite volume of water. This increase is also in good agreement (within a factor of 2 to 3) with the theoretical model analysis given above, further confirming the FMRH effect in a phantom system.

Selection and Synthesis of SPM Nanoparticles

There are many ways to synthesize the nanoparticles suitable for use in the present embodiments. These nanoparticles may have widely differing chemical compositions and particle sizes, and will still meet the present requirements for FMRH thermal cancer therapy. In spite of the many methods that are available, and while not wishing to be held to any particular method or technique, a few exemplary methods of synthesis will be discussed in this section.

Wet chemistry and sol-gel methods comprise a more traditional approach to nanoparticle synthesis. For the synthesis of oxide materials, a conventional method is to combine the ions in an aqueous solution, further provide a capping group, and then adjust the pH to precipitate the particles. A modification of that procedure that produces narrower size distributions involves the use of a surfactant and an additional solvent(s), thus limiting the room which the nanoparticle has to grow. In one embodiment of the sol-gel method, metal ions are incorporated in a gel, which is formed by the heating of an aqueous citrate solution. This gel is then heated first to a temperature high enough to drive excess water from the gel, and then heated far higher (typically over 1,000° C.) to burn off the organic component leaving behind metal oxide nanoparticles.

There are a number of vapor phase nanoparticles synthesis techniques. Several of these techniques use solid precursor materials. Inert gas condensation, where solids are heated to evaporate, and then an injection of cold, inert gas into the reaction chamber condenses the gas into nanoparticles. Pulsed laser ablation, uses a pulsed laser sequence to vaporize solids, rather than using heat. Spark discharge uses an electric arc to vaporize portions of the electrode material to subsequently form nanoparticles. Ion sputtering techniques can also be used to vaporize materials to form nanoparticles upon condensation. A number of vapor phase synthesis techniques use liquid, solution or vapor phase precursors. The most common, current commercial method is flame synthesis, where vapor precursors are introduced into a flame, making nanoparticles; primarily used for carbon black or metal oxides. Similar to flame synthesis is flame spray synthesis, where the liquid or solution precursor material is directly introduced to the flame. Chemical vapor synthesis builds upon chemical vapor deposition technology, to use the same vapor phase precursors and decompose them in a hot zone to form nanoparticles. Spray pyrolysis is a method which is similar to chemical vapor synthesis, with the major difference being that the precursors are injected as aerosol. In thermal plasma synthesis, the precursors are injected into a thermal plasma, which generally decomposes the precursors to atoms, which then reform into nanoparticles.

One exemplary method, the laser pyrolysis technique was established as an alternative approach to synthesize nanoparticles with the advantages over other chemical synthesis approaches in pioneering work by a prior art investigator. The advantages are (a) small particle size, (b) a narrow particle size distribution, and (c) a near absence of aggregation. By implementing the combinatorial material synthesis capability, the combinatorial laser pyrolysis (CLP) system enables the development of various nanoparticles with different chemical compositions and nano-sizes meeting different requirements of a variety of applications.

Figure 9A:
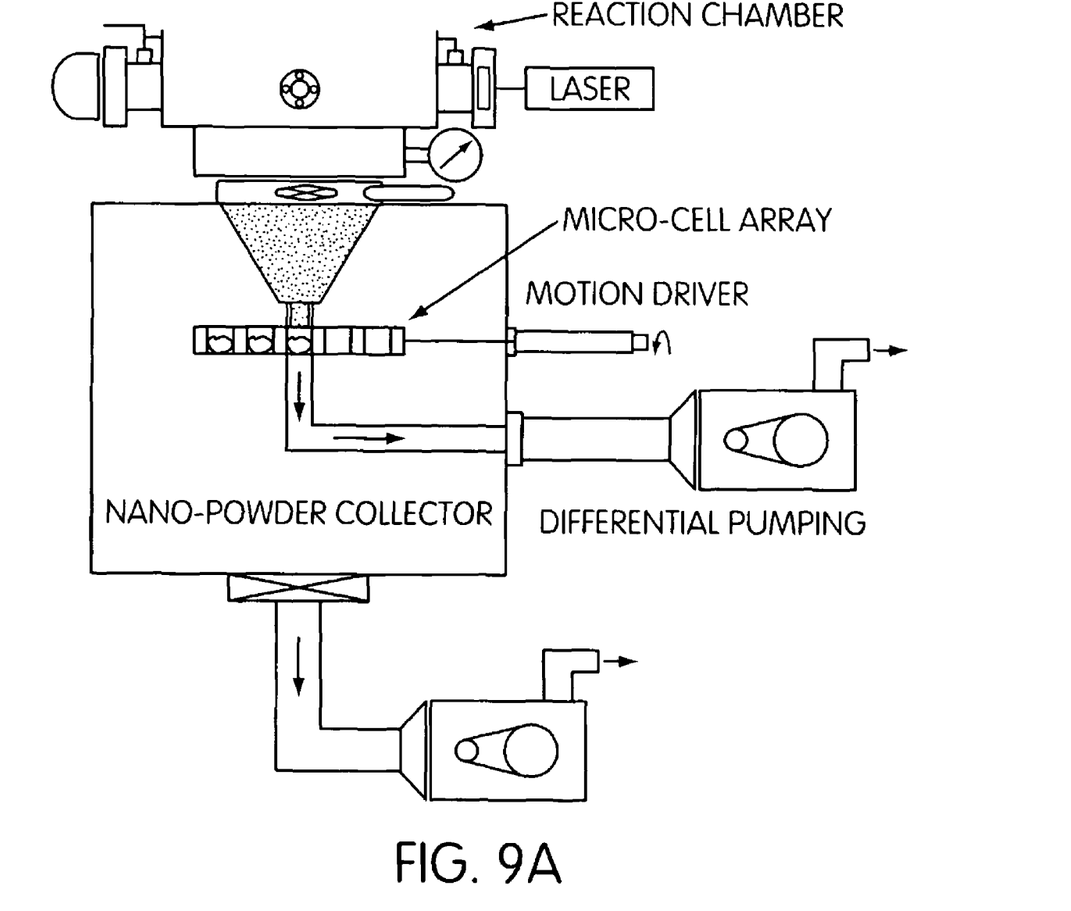
FIGS. 9A-D are, respectively, (a) a schematic of a nanoparticle synthesizing system, and (b) a picture of such a system; (c) a TEM image of exemplary $TiO_2$ nanoparticles prepared by CLP, where the inset in the picture is a high resolution image of the crystal structure; and (d) a TEM image of YIG nanoparticles prepared by CLP, where the image to the right of the picture right shows the crystal structure.
Figure 9B:
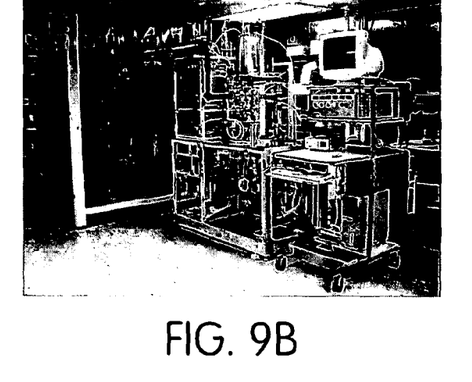

FIGS. 9A-D show the CLP system. A $CO_2$ laser is used to heat gas molecules delivered by a multi-precursor ink-jet chemical vapor delivery system. Using a laser's narrow spectral width allows efficient coupling between the light and molecular precursors that have exact wavelength of absorption (over 15% of the laser power can be consumed). The CLP system has two computer controlled source injectors for delivery of organometallic precursors, allowing precise control of the composition of the produced nanoparticles. The vaporized precursors, mixed with carrier gas and heat adsorption, gases are heated by the laser beam in the reaction chamber forming a flow of nanoparticles. Oxygen ($O_2$) or air is introduced into the reaction chamber for the synthesis of oxides, while air-sensitive particles can also be synthesized as the system is capable of maintaining a pressure of about $1 \times 10^{-6}$ Torr. The nanoparticles are collected by means of micro-cell array with differential pumping (as illustrated in FIGS. 9A-B). With the motion control, each cell collects the only the nanoparticle samples generated under different experimental conditions (leading to different sizes and compositions of particles). The structure and size of powders are subsequently characterized using transmission electron microscopy (TEM) and X-ray diffraction spectroscopy.

Figure 9C:
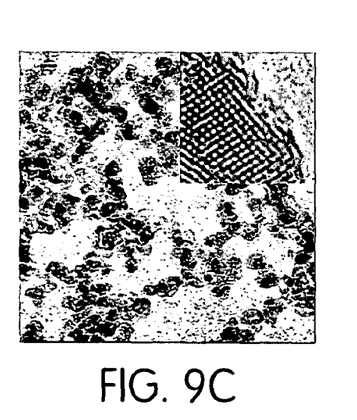
Figure 9D:
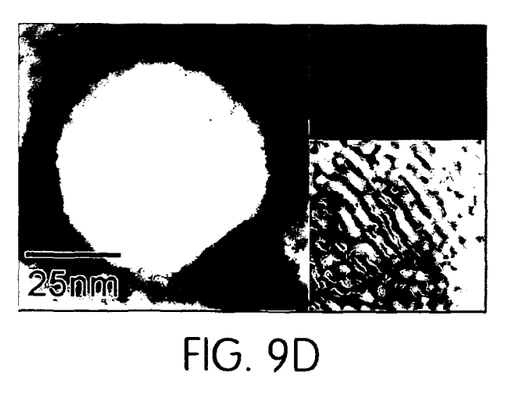
Figure 10:
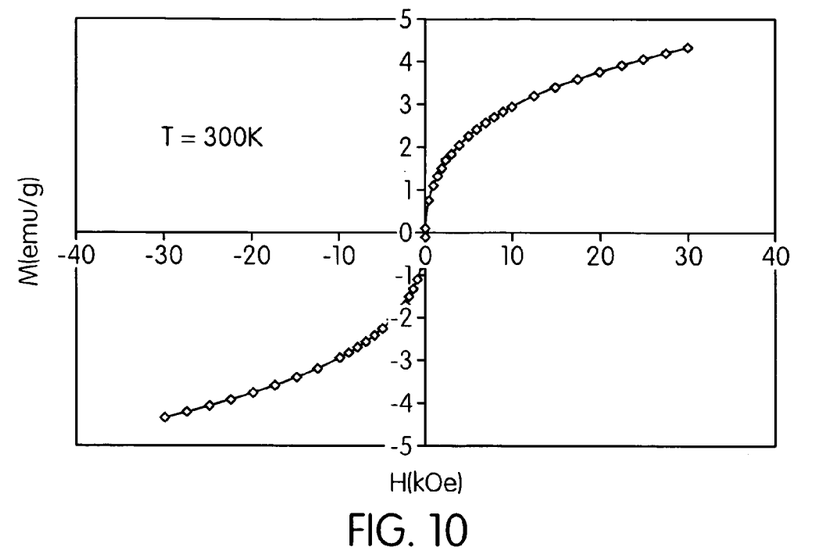
FIG. 10 is a plot of magnetization versus applied magnetic field of YIG nanoparticles.
Figure 11A:
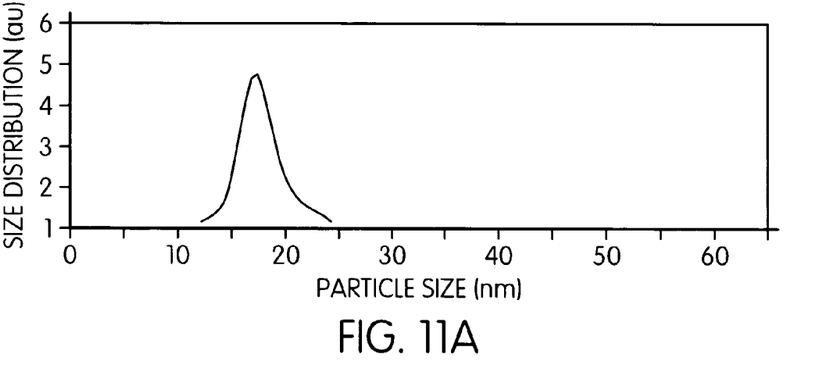
FIGS. 11A-B are respectively, (a) a plot of size distribution of YIG nanoparticles made by the present inventors using CNP, and (b) commercially available nanoparticles.
Figure 11B:
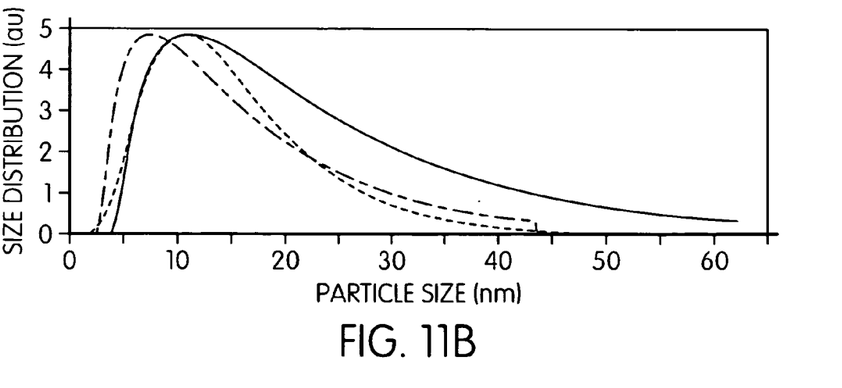

FIGS. 9C-D also show TEM and SEM images of $TiO_2$ and YIG nanoparticle synthesis using the present system. The magnetic measurement of YIG nanoparticles (see FIG. 10) shows well behaved super-paramagnetic properties. The FMR of nano-particles ($\gamma$-$Fe_2O_3$) has been measured at 2.4 GHz. The size distribution of synthesized particles (shown in FIG. 10) is much narrower than that of commercially available particles. This present technique enables methods to quickly vary the composition and size of nanoparticles for efficient heating.

While the magnetic moment and particle size of the YIG nano-particles can be fine-tuned using the CLP methodology to optimize the function of the YIG in cancer treatment for example with different particle sizes, a very limited selection of particle sizes and compositions may be chosen for relevant study. $C_6H_8Fe(CO)_3$ and $Y(OC_4H_9)_3$ may be used as precursors for Fe and Y, respectively. The organometallic precursors may be dissolved into hexane, for example, and delivered into the reaction chamber through the CVD injectors. The particle size may then be controlled in a patented process by varying experimental parameters, such as the flow of the precursor, and the pressure of the reaction chamber.

Surface Modification and Suspension of Magnetic Nanoparticles in Bio-Compatible Solutions For delivery methodologies not involving direct injection of the particles into the tumor, the particles should not be captured and passivated by the body's immune system. Additionally, nanoparticles tend to agglomerate if not properly treated to prevent these interactions. Such treatment may include pH adjustment of the suspending fluid, use of van der Waals bound surfactants, or covalent linkage of such surfactants.

After examining the use of uncoated and dextran coated particles, prior art investigators found that ferrofluids of magnetite particles coated with aminopropyl trimethoxysilane were superior for their hyperthermia cancer therapy system. Some basic methods for silane coating have been disclosed. Based on this work, the present inventors have designed a coating procedure to modify the surfaces of magnetic nanoparticles for bio-compatible solutions. For example, $(MeO)_3SiCH_2CH_2CH_2NH_2$ may be dissolved in de-ionized water under ultrasonic conditions to undergo hydrolysis of the three labile methoxy groups to form $(HO)_3SiCH_2CH_2CH_2NH_2$. Further ultrasonic mixing fosters oligomer formation: $(HO)_2Si(R)$—O—$(R)Si(OH)$—O—$Si(R)(OH)_2$, $R=CH_2CH_2CH_2NH_2$. Addition of a pre-prepared mildly basic, colloidal nanoparticle (YIG) solution without aggregates allows the formation of hydrogen bonds between the —OH groups of both the nanoparticles and the Si oligomers. Covalent linkage (Fe—O—Si) is obtained by the loss of water from these H-bonds upon heating (ca. 60° C.). The coated particles may be isolated via gel filtration chromatography.

Another embodiment of surface modification is to prepare a dextran type shell Based on reports published in literature, magnetic YIG-dextran particles may be prepared by suspending YIG nanoparticles in de-ionized water with ultrasonic mixing and pH adjustment with acetic acid or ammonium hydroxide, depending upon charge type required for the specific applications. An equal volume of a 20% (w/v) dextran (e.g. 40 kDa) solution in deionized water may be mixed with the YIG solution and kept slightly above room temperature (about 35° C.) for about. 15 minutes under ultrasonic mixing to allow coating occur. The YIG-dextran particles may then be separated from unbound dextran by gel filtration chromatography on Sephacryl S-300 with pH 6.5 (acetic acid/sodium acetate) buffer. The purified YIG-dextran particles collected in the void volume are expected to have a concentration of about 7-10 mg/ml. Such a coating will improve solubility, chemical stability and reduce toxicity.

A third method involves coating the nanoparticles with polyethylene glycol derivatives to decrease immune system response. For example, particles previously coated with 3-aminopropylsilane may be further treated methoxypoly (ethylene glycol) succinimidyl propionate at a pH of about 6 for about 72 hours at room temperature with ultrasonic mixing. Other potential methods include reaction with silane conjugated PEG in toluene (4 h at 50° C.). The coated nanoparticles may then be further modified to incorporate a targeting functionality, such as a molecule which will bind to a receptor on the membrane of the cancer cell.

In one embodiment, the coated nanoparticles are chemically modified to incorporate folic acid as a targeting agent (as done, for example, in a KB cell model, modeling cancer cells which overexpress the folate receptor). NHS-folate may be reacted with the terminal amine functionality on the coated nanoparticles, and fluorescein similarly covanlently linked to the nanoparticles to enable detection during cell culture studies.

In a slightly different embodiment, the coated nanoparticles may be further chemically modified for direct covalent linkage to the pRNA either through the formation of an ester linkage with the terminus of a PEG group, or coupling to an amino group of an aminosilane coated particle.

What is claimed is:

1. A system for carrying out a ferromagnetic resonance heating treatment of a tumor, the system comprising:
    a volume concentration of super paramagnetic particles adapted to be contained within the interior of the tumor, the concentration ranging from about 0.1 to about 1 percent;
    a magnetic field source configured to deliver a gradient DC magnetic field to the region of the tumor; and
    an energy source configured to deliver to the tumor an RF field at a frequency ranging from about 100 to 200 MHz.

2. The apparatus of claim 1, wherein the super paramagnetic particles are selected from the group consisting of maghemite ($\gamma$-$Fe_2O_3$) based compounds, and yttrium iron garnet ($Y_3Fe_5O_{12}$) based compounds.

* * * * *